(12) United States Patent
Miethke

(10) Patent No.: US 9,572,965 B2
(45) Date of Patent: Feb. 21, 2017

(54) ADJUSTABLE HYDROCEPHALUS VALVE

(71) Applicant: Christoph Miethke, Potsdam (DE)

(72) Inventor: Christoph Miethke, Potsdam (DE)

(73) Assignee: C.MIETHKE GMBH & CO KG, Potsdam (DE)

( * ) Notice: Subject to any disclaimer, the term of this patent is extended or adjusted under 35 U.S.C. 154(b) by 38 days.

(21) Appl. No.: 14/643,828

(22) Filed: Mar. 10, 2015

(65) Prior Publication Data

US 2015/0182734 A1 Jul. 2, 2015

Related U.S. Application Data

(63) Continuation-in-part of application No. PCT/EP2013/002713, filed on Sep. 10, 2013.

(30) Foreign Application Priority Data

Sep. 11, 2012 (DE) .................. 10 2012 017 886

(51) Int. Cl.
*A61M 27/00* (2006.01)

(52) U.S. Cl.
CPC ................ *A61M 27/006* (2013.01)

(58) Field of Classification Search
CPC ................ A61M 27/00; A61M 27/006
See application file for complete search history.

(56) References Cited

U.S. PATENT DOCUMENTS

| 4,443,214 A | 4/1984 | Marion |
|---|---|---|
| 4,540,400 A | 9/1985 | Hooven |
| 4,551,128 A | 11/1985 | Hakim et al. |
| 4,673,384 A | 6/1987 | Marion |
| 4,769,002 A | 9/1988 | Hooven |
| 5,637,083 A | 6/1997 | Bertrand et al. |
| 5,843,013 A | 12/1998 | Lecuyer et al. |
| 6,840,917 B2 | 1/2005 | Marion |
| 7,422,566 B2 | 9/2008 | Miethke |
| 8,298,168 B2 | 10/2012 | Bertrand et al. |
| 8,517,974 B2 | 8/2013 | Barr |
| 8,813,757 B2 | 8/2014 | Prisco et al. |
| 2005/0055009 A1 | 3/2005 | Rosenberg |

(Continued)

FOREIGN PATENT DOCUMENTS

| DE | 69808558 | 6/2003 |
|---|---|---|
| DE | 10358145 | 7/2004 |

(Continued)

*Primary Examiner* — Tatyana Zalukaeva
*Assistant Examiner* — Benjamin Klein
(74) *Attorney, Agent, or Firm* — Nils H. Ljungman & Associates

(57) ABSTRACT

An adjustable hydrocephalus valve for pressure equalization of the cerebrospinal fluid in the cranium of a hydrocephalus patient. The valve is adjustable to change the opening and closing pressure of the valve. The valve housing has a cover portion that can be depressed to thereby disengage a locking device to permit adjustment of the valve. The cover portion bulges outwardly, but bulges inwardly when depressed. The cover portion snaps when moved between the outward bulge and the inward bulge to thereby generate an audio and/or visual signal indicating that the cover portion has been switched from the outward bulge to the inward bulge, and vice versa.

13 Claims, 7 Drawing Sheets

(56) References Cited

U.S. PATENT DOCUMENTS

| | | | |
|---|---|---|---|
| 2007/0093741 A1* | 4/2007 | Miethke | A61M 27/006 |
| | | | 604/9 |
| 2012/0197178 A1 | 8/2012 | Prisco et al. | |
| 2012/0302937 A1 | 11/2012 | Barr | |
| 2013/0066253 A1 | 3/2013 | Bertrand et al. | |
| 2013/0085441 A1 | 4/2013 | Aihara | |
| 2014/0005569 A1 | 1/2014 | Miethke | |

FOREIGN PATENT DOCUMENTS

| | | |
|---|---|---|
| DE | 60024437 T2 | 7/2006 |
| DE | 60315924 | 5/2008 |
| DE | 102008030942 | 1/2010 |
| DE | 102005013720 | 8/2012 |
| EP | 0421557 | 4/1991 |
| EP | 0688578 | 12/1995 |
| EP | 1243826 | 9/2002 |
| EP | 1457231 | 9/2004 |
| EP | 1604703 | 12/2005 |
| EP | 1642613 | 4/2006 |
| EP | 2055227 | 5/2009 |
| EP | 2420284 | 2/2012 |

\* cited by examiner

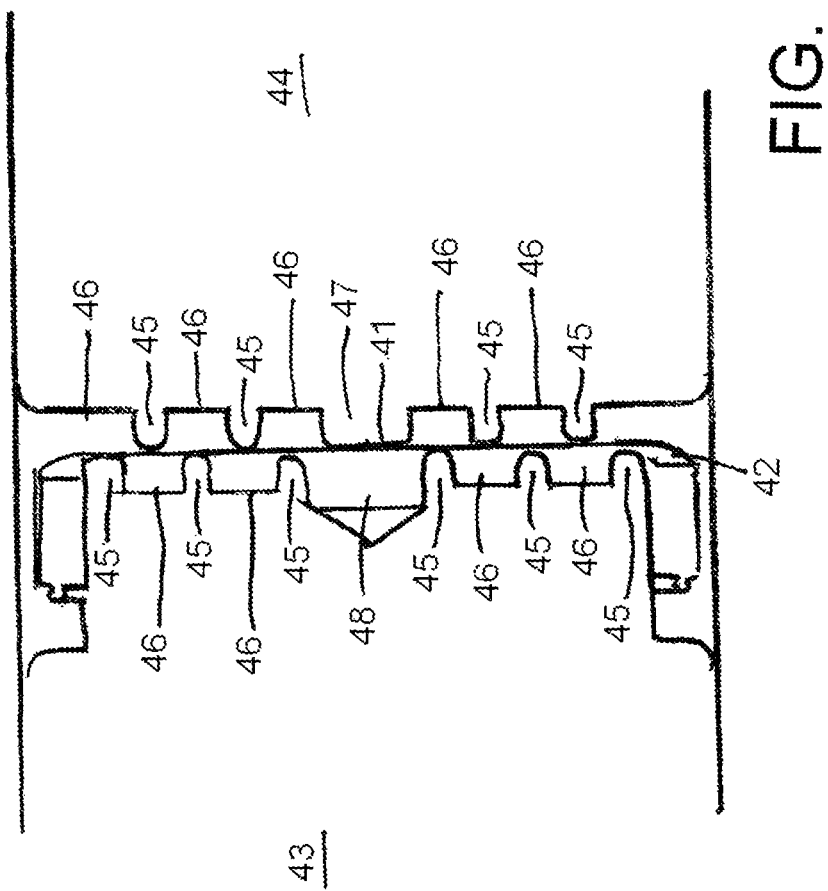

ADJUSTABLE HYDROCEPHALUS VALVE

CONTINUING APPLICATION DATA

This application is a Continuation-In-Part application of International Patent Application No. PCT/EP2013/002713, filed on Sep. 10, 2013, which claims priority from Federal Republic of Germany Patent Application No. 10 2012 017 886.7, filed on Sep. 11, 2012. International Patent Application No. PCT/EP2013/002713 was pending as of the filing date of this application. The United States was an elected state in International Patent Application No. PCT/EP2013/002713.

BACKGROUND

1. Technical Field

The present application relates to an adjustable hydrocephalus valve.

2. Background Information

Background information is for informational purposes only and does not necessarily admit that subsequently mentioned information and publications are prior art.

The present application relates to an adjustable hydrocephalus valve to equalize the pressure of the fluid in the cranium of a hydrocephalus patient.

Hydrocephalus patients have the following medical problem:

In the cranium, the brain is surrounded by a special liquid called cerebrospinal fluid (CSF) or liquor. This liquor is continuously produced and reabsorbed in equal amounts. In the illness hydrocephalus (also called water on the brain), this equilibrium is disrupted and more liquid is produced than is reabsorbed. Because the interior of the skull represents a closed vessel, the result is an increase in volume. In infants, the seams in the skull cannot grow together and close, and, in adults, the internal pressure in the skull increases. Therefore there are two types of hydrocephalus: adult and infantile.

Hydrocephalus treatment initially comprised simply draining the liquor. This drainage was effected by means of a simple hose connection between the skull and a large venous blood vessel or by a corresponding connection between the skull and the abdomen via a hose. It was quickly determined, however, that the pressure in the skull must or should maintain a certain physiological value if other complications are to be prevented or minimized.

A number of different types of valves are known that are installed in the drain for the liquor, and by means of which the pressure of the liquor can be adjusted. Valves of this type are implanted under the skin in the vicinity of the head. The valves are designed to open at a certain critical pressure and to release the flow of liquor. By means of a line—which is also implanted under the skin—the liquor is drained into the upper vena cava or into the abdominal cavity.

But a satisfactory solution has not yet been achieved with known valves.

The adjustment to the patient in question, i.e. to the particular application case, is lacking.

Valve developments that allow an adjustment are already known.

The valves in question are implanted in the patient and, for example, drain the excess liquor from the patient's skull via a tube line, which is likewise implanted, and empty, for example, into a vena cava or into the abdomen. The valve pressure is thereby determined by a spring, wherein the spring is adjusted by means of a mechanism that has a pivoting or rotating part that is moved from outside by pivoting or rotating the magnets, so that the spring is wound up or released.

The known valves have a more or less flat construction. The objective of the flat construction is to prevent or minimize bumps or protuberances on the patient's head to the maximum extent possible as a result of the implant procedure.

Some valves include, for example, the Codman Medos valve.

This valve is a ball valve with a spring-loaded ball. The valve is adjusted by changing the position of the spring. The spring presses with one end on the valve ball. With the other end, the spring is braced against an abutment. In this model, the height of the abutment can be adjusted by rotation. The height can be adjusted because the abutment is rotational and is provided on top with an inclined or step-wise edge along which the spring glides. The adjustment range of the abutment is limited to a rotational movement of the abutment of maximum one hundred eighty degrees.

This leads to inaccuracies in the adjustment. In addition, a slight unintended rotational movement of the abutment can already lead to considerable valve modifications.

The Sophysa valve is also one of the known valves.

Even the manufacturer of this valve warns that the hydrocephalus patient should avoid or minimize coming into contact with permanent or substantially permanent magnets in toys, headsets, loudspeakers and electromagnetic fields of the type that are emitted by electric motors, electric shavers, hair dryers, switches, etc. This warning from the manufacturer comprises a warning against most areas of everyday life. As a person is unable nowadays to evade exposure to such things, proposed solutions of this kind are generally impractical.

In the meantime some efforts have been made to improve the valves. An example of a valve is disclosed in U.S. Pat. No. 7,422,566 (inventor Christoph Miethke), which patent is incorporated by reference herein.

Some valves retain the known constructional design and have the objective to increase the safety of such valves.

In some valves, greater safety is achieved in two ways.

The first way includes an adjustment of the spring. In this regard, a possibly large adjustment path is provided, which is accompanied in a change in the spring loading. This means that a greater adjustment path is provided for a comparable modification range of the spring loading. To the extent in which the adjustment path becomes larger, the above expressed danger of an unwanted adjustment is reduced.

Possibly, the accuracy of the adjustment is simultaneously or substantially simultaneously increased as the adjustment travel becomes greater.

Some valves comprise magnetically actuated locking as the other way to greater security.

The possibility for a larger design of the adjustment path results from the modification of the location of the spring. In some valves, the spring is placed such that the plane of movement of the spring, when it is adjusted, lies parallel or substantially parallel to the plane, in which the pivotable movement or rotational movement of the rotating part/rotor takes place. In this regard, the parallelism also occurs if the planes coincide.

As a result of the possible arrangement of the spring, the spring can move in the direction in which the valve housing has the largest dimension. This is in the direction of the flat side.

The spring is possibly a spring bar that is arranged in a pivotably movable manner and whose one end is longer than the other end. The shorter end is in operative connection with the one valve ball or valve shutter of the valve, and the longer end enables the greater adjustment path and cooperates with the described adjustment mechanism. A sliding operative connection, known per se, is provided between the spring and the rotationally movable or pivotably movable part. This means that the spring slides on a surface of the rotationally movable or pivotably movable part of the adjustment mechanism.

The use of a spring bar that is designed as a two-armed lever arm is possible. The two-armed lever arm is hinged.

The operative connection with the valve ball or the valve shutter is created by the short end sliding against the valve ball or pressing against the valve shutter.

The operative connection with the adjustment mechanism is formed such that a sliding surface for the shorter lever arm is provided on the rotationally movable or pivotably movable part/rotor, and is designed as a curved path, on which the spring bar slidingly fits.

In some valves, the curved path runs in the circumferential direction and in the radial direction to the rotationally movable or pivotably movable part. The circumferential angle to the pivotably movable or rotatably movable part comprises for example at least three hundred degrees.

The spring defining the valve pressure can slide on the curved path in a pivoting direction/rotational direction or in both pivoting directions/rotational direction. The direction of movement is the result of the direction of rotation or pivoting direction of the rotatably movable or pivotably movable rotating part/rotor.

The rotatably movable rotating part/rotor can optionally be also moved further in the same rotational direction and nonetheless return to the adjustment beginning. This is achieved in that a connection is provided between the start of the curved path and the end of the curved path to the rotatably movable or pivotably movable part.

The rotatably movable or pivotably movable rotating part/rotor is seated on an axle/pivot/bolt that is formed integrally with the flexible cover or base of the housing. With the axle/pivot/bolt, the rotating part/rotor is rotatably movable or pivotably movable in the housing of the valve.

The spring defining the valve pressure slides on the rotatably movable rotating part/rotor and possibly has an angular shape. The two lever arms of the two-armed lever arm are at an angle to each other that is possibly less than one hundred eighty degrees and can also be less than ninety degrees.

The spring defining the valve pressure can have any cross section. Circular and rectangular shapes are possible. A spring with a leaf-shaped or wire-shaped cross section is possible.

A pin/axle/bolt, whose ends engage in suitable recesses in the valve housing or in the valve cover or valve base, is suitable for example for the rotatably movable or pivotably movable mounting of the spring that defines the valve pressure. The ends of the pin can also be pointed, such that the bar rotates on the tips in the recesses. This procedure is technically and economically possible.

To fasten the pin to the spring, a welded or soldered connection is suitable, as well as other types of connections.

For the spring defining the valve pressure to function it is possible if the long lever arm on the rotatably movable part or pivotably movable part (rotating part/rotor) of the adjustment mechanism is controlled. For that purpose this rotating part/rotor at the same time can control the spring defining the valve pressure on at least one side. On the other side the guide can be formed for example by a disk or by a membrane or by a housing cover or housing floor.

On the side of the valve ball it is possible if large area contact occurs between the spring defining the valve pressure and the valve ball. If the spring defining the valve pressure is not capable of touching this large area then a metal sheet can be fixed to the relevant end of the spring. The metal sheet is optionally welded on or soldered on or fastened in another way.

The rotating part/rotor is usually moved with magnets that are embedded into the rotating part/rotor. Hereinafter, the rotating part/rotor and the spring defining the valve pressure are referred to as the adjustment mechanism of the implanted valve. For adjusting the valve pressure an adjustment mechanism that is also provided with magnets is placed externally on the skin of the patient. These magnets of the externally placed adjustment mechanism interact with the magnets of the rotating part/rotor in the implanted valve, such that a rotation/pivoting motion of the externally placed adjustment mechanism brings about a rotation/pivoting motion of the rotating part/rotor arranged in the implanted valve. This results in an adjustment of the spring defining the valve pressure, linked with a change in the valve pressure.

The adjustment mechanism can also be involuntarily adjusted if the patient enters into the effective range of strong magnetic fields.

This led to the wish to lock the adjustment mechanism in each position. Various proposals have been made for locking.

Known proposals again use magnets for locking.

Other proposals use spring forces and frictional forces for locking.

In one proposal a housing in the locked state presses with cams in a friction locking manner onto the rotatingly movable rotor/rotating part that carries the oblique surface or staircase-shaped tiered surface, on which the above-described spring slides. For unlocking, the housing has to or should be curved in such a manner that the cams lift off from the rotor/rotating part. After the cams have lifted off, the rotor/rotating part can be adjusted with an adjustment mechanism that is located externally on the skin of the patient. This adjustment mechanism possesses magnets that interact with other magnets that are arranged in the rotor/rotating part.

In another proposal, the spring force of a curved housing cover is used for unlocking. The cover pulls the rotor/rotating part against it with its force resulting from the curvature, such that, in the locked state, the rotor/rotating part is friction-locked with the housing cover. Here, the rotor/rotating part is rotationally movably/pivotably movably seated on an axle/bolt provided on the housing cover.

For unlocking, the housing cover is deformed, such that the rotor/rotating part lifts off from the housing cover, the friction lock to the cover no longer exists and the rotor/rotating part can be pivoted with the help of an adjustment mechanism that is externally placed on the skin of the patient. The adjustment mechanism possesses magnets that are inserted into the rotor/rotating part.

Depending on the rotational/pivotable direction, the rotationally movable rotating part/rotor tightens or releases the spring that defines the valve pressure and which slides on the rotating part/rotor. In this regard, the spring defining the valve pressure slides on a curved path of the rotating part/rotor. At the same time the spring defining the valve pressure presses on the valve ball of the valve, such that a desired modification of the closing pressure of the valve ball or the valve occurs.

The valve ball interacts with a conical opening in the housing of the valve. In some valves, this opening is located on the inlet side of the valve.

The magnets possibly have a compact design, for example pin magnets are used. The small magnets also contribute to the compact dimensions of the valve.

The valve adjustment mechanism provided externally on the skin of the patient can likewise be designed with extremely small dimensions. In some valves, use is made of a reduced diameter and a possible shape of the adjustment device, namely designed in the shape of a pen, similar to a ballpoint pen. This allows the adjustment device to be handled as a pen or ballpoint pen, e.g. by carrying it in a breast pocket. At the same time the mechanism of a ballpoint pen is utilized in order to move the magnets provided in the head of the adjustment mechanism backwards or forward lengthways along the pen (with the applied pen, toward the head of the patient or toward the valve). In the vertical position of the pen, that means raising and lowering.

The pen-shaped adjustment device that is applied externally on the skin of the patient optionally possesses on the front end a cap, on which the adjustment device is placed. Loosely placing the adjustment device should automatically cause the magnets to center the adjustment device above the rotor/rotating part of the valve.

Once the adjustment device that is located externally on the patient has been centered on the implanted valve, provision is made for an elastic deformation of the implanted valve so as to unlock the rotating part/rotor. The above described adjustment is then carried out.

OBJECT OR OBJECTS

An object of the present application is to improve the technology. In this regard the present application takes into account that the valve and its manipulation are still capable of improvement.

SUMMARY

According to the present application, this is achieved with the valve disclosed herein.

It should be noted that the valve emits a signal on unlocking and/or locking. Signals may also be utilized when controlling the position of the rotatably movable or pivotably movable rotating part/rotor. The signals can be acoustically and/or optically and/or electronically perceptible. The signals essentially safely ensure or promote a correct placement of the adjustment device. The actual position of the valves and the subsequent correct change of position can be undertaken following a correctly assessed placement.

Electronic signal generators can optionally be used.

Electronic signal generators can produce the signal, as desired, in optical and/or acoustic form or as a perceived signal. This includes a remote transmission of the signal generated in the subcutaneously located valve to an externally located signal receiver and a signal conversion in the externally located signal receiver.

Passive transponders in the valve can be possible as the signal generator. The passive transponders respond to signals that are input from outside, and then spontaneously generate a signal toward the exterior.

The signal is in one possible embodiment mechanically generated. Clicking noises are also possible. The clicking noises result for example by the use of spring steel or another elastic material, which on pressing suddenly bulges, thereby creating a noise.

The clicking noises result for example by the use of elastic materials with a relatively high deformation force or a high relative resilience. However, the configuration of the material is in one possible embodiment selected so as to allow a manual actuation. The selection includes not only the material per se, but also its shape. The higher the strength of the material the thinner the material can be selected in order to permit the manual actuation. Spring sheets are in one possible embodiment chosen with a thickness of 0.5 millimeters at most, in another possible embodiment 0.4 millimeters at most and in yet another possible embodiment 0.3 millimeters at most.

According to the present application the elastic material is made to change shape and subsequently suddenly released, such that, depending on the type of deformation, the material can suddenly deform further or suddenly recover its original shape. Every reasonable biocompatible elastic material comes into consideration for the material. They include metals as well as plastics and also composites. The spring sheets are optionally made of the same material as that of the spring that defines the valve pressure. Titanium (titanium alloys) is in one possible embodiment used for the spring sheets.

As no permanent absolute elasticity exists, materials should be used that during the lifetime of a valve suffer a maximum of fifty percent residual deformation from the deformation described in the present application, in one possible embodiment a maximum of thirty percent residual deformation, in yet another possible embodiment a maximum of ten percent residual deformation, and in still a further possible embodiment a maximum of five percent residual deformation, wherein the indicated percentages refer to the degree in which the shape recovery after the last noise-generating deformation of the spring steel during the lifetime of the valve is reduced with respect to the shape recovery after the first noise-generating deformation.

The sheet metal material is in one possible embodiment selected from titanium (titanium alloys) or from the same metal, from which the housing of the hydrocephalus valve is made. This material is biocompatible. For the spring sheets made of titanium or from the same metal as the valve housing, the elasticity/residual deformation requirement is the same as for steel spring sheets.

Optionally, rod-shaped or leaf-shaped springs/spring sheets are used for the noise-generating deformation. In addition, the shape of the springs/leaf springs also influences how the noise-generating deformation is produced.

The noise-generating deformation can be a simple bending or shape recovery after a simple bending. In this regard the leaf spring can have a planar or another initial shape prior to deformation. An indentation of the leaf spring or a shape recovery of the leaf spring from the indentation is in one possible embodiment utilized as the noise-generating deformation. In this regard the leaf spring can also have a planar or another initial shape.

The deformation of the leaf spring requires or desires a corresponding available space in the valve. Here the leaf spring is possibly a component of the valve housing. The leaf spring in one possible embodiment simultaneously or substantially simultaneously forms the valve cover. The leaf spring that forms the valve cover can then also be designated as a membrane. According to the present application, the valve cover may not be part of the valve that lies uppermost; rather it is the part of the implanted valve that is implanted in the patient such that its valve cover corresponds with an adjustment device that is placed externally on the skin of the patient. In this regard, the valve is not bound to an implantation under the scalp of the patient. Even when that is the usual implantation point, the valve can also be implanted at another point of the body.

The leaf spring optionally also forms an accessory for a valve.

A circular leaf spring with a bulging structure is in one possible embodiment provided as the initial shape which is manually pressed in. The bulging structure that forms the initial shape is in one possible embodiment produced by cold forming.

Circular leaf springs that are pressed in are known in hydrocephalus valves. However, the known leaf springs do not make any noise.

A strained state in the leaf spring is decisive for the noise generation.

With the manually pressed-in bulge in the leaf spring, unlike when a planar leaf spring is pressed in, there results a possible force/travel characteristic curve. On pressing, the characteristic curve initially rises. Here, due to the bulging structure to be pressed in, the resistance against the pressing increases more strongly than when a planar leaf spring is deformed. When a certain force is exceeded and a certain deformation state is reached, the curve decreases steeply and abruptly. At the point of inflection of the force/travel characteristic curve, there results the snap-through effect known in the field of mechanics. This means that the leaf spring snaps through to the other side and results in an acoustic and haptic noise that is referred to as a "click." This effect is utilized in toys, known as "clickers." The snap through is also perceptible. This effect is also used when training/dressing animals. In such cases the device is called a clicker.

Technologically, this noise generation is also known in snap-action switches, flip switches and toggle switches. Here, the aim is not that of generating noise, rather the sudden contact of the switching surfaces in order to avoid, restrict, and/or minimize current spikes from the switching operation.

The snap-through of the leaf spring produces a bulge on the opposite side of the leaf spring.

At the end of the loading force there are two possibilities, variant (A) and variant (B), which are discussed in the following several paragraphs.

Variant (A)—In one variant there results a stable state. After the snap-through, the bulge remains on the side on which it was formed. This means that the leaf spring has two stable bulge states: the bulge prior to deformation and the bulge after deformation. In order to achieve a shape recovery after a deformation, a mechanism is in one possible embodiment provided, with which the bulge can again be pressed in. The mechanism can generate a counter pressure against the bulge that was formed, thereby initiating the shape recovery. The axle, on which the rotating part/rotor is seated, and a spring acting on the axle can be optionally utilized for this purpose.

In addition, the rotating part/rotor can also be used for the shape recovery. This applies in one possible embodiment to the case where, for the locking process, the rotating part/rotor is brought into a frictionally locked contact with the valve cover and when the adjusting part/rotor with the associated axle is pressed by a spring in the direction of the valve cover, the spring being independent of the valve cover. This spring is then in fact compressed on unlocking. On locking, however, the pressure is again taken up by this spring, because the adjustment device that is located externally on the skin of the patient is removed. The spring can then not only effectuate the locking process, but also simultaneously or substantially simultaneously initiate the shape recovery of the bulge that resulted from the first deformation process. The jolt does not have to be executed with the force required or desired for the first deformation step.

A state of strain in the leaf spring which resulted from the first deformation step substantially supports the shape recovery. In this regard it is possible if the leaf spring is designed as a diaphragm. Even more favorable states of strain result if the leaf spring is circular in shape, and is deep drawn into a permanent or substantially permanent shape that forms a stepped bulge.

The bulge structure according to the present application has the further possibility of additional spring characteristics, of greater stability and higher strength, such that even a somewhat off-centered application of force is innocuous when unlocking and adjusting the valve.

Moreover, the sound from a snap-through inventively corrugated or stepped deep-drawn leaf spring is perceived to be more congenial than the sound from a snap-through unstepped/uncorrugated leaf spring.

Moreover, the energy expended for the shape recovery which was required or desired for the first deformation in order to press together the spring that caused the frictional lock in the locking step is dispensed with.

It is also possible for the shape recovery if the housing cover has two walls, wherein the abovementioned leaf spring forms the outer wall and the second, inner wall limits the deformation of the first outer wall/leaf spring. This limitation can also be called an abutment, because the first wall bears against the inner wall in the first deformation.

The deformation of the outer wall is in one possible embodiment ended directly after the noise generation with the help of the second, inner wall. In this way the spring force required or desired for the initiation of the shape recovery is also reduced.

Similarly, the shape recovery in one possible embodiment ends with the generation of noise. This brings additional security to the correct valve adjustment.

Variant (B)—In the second variant, a leaf spring with a cold molded-in bulge structure is used in an otherwise identical construction as in variant (A). The leaf spring of the variant (B) differs from that of the variant (A) in that the leaf spring does not need or desire a jolt for it to recover its shape at the end of the deformation. This is due to the fact that the strain generated by the cold forming, together with the strains from pressing in the bulge structure, are great enough to effectuate the automatic shape recovery, but nonetheless still showing the effect of the noise-generating snap-through.

This leaf spring has a possible advantage over the leaf spring according to variant (A), in that it facilitates the task and, in the possible case of plastic deformation due to operating error, offers a reserve or security that the leaf spring reforms itself into the desired shape. This spring was tested with a load of ten kilograms. A doctor most likely would not inadvertently cause a greater load when adjusting the valve pressure. Ultimately, the first, outer wall of the housing cover which forms the leaf spring has in fact itself undergone a plastic deformation. The force/travel characteristic curve has changed to such an extent that the first wall of the housing cover has generated a noise under lesser force then previously, but has still effectuated the desired unlocking effect and after the relief of the strain has again recovered its shape to an extent that the locking occurs and subsequent unlocking and locking steps were not disturbed.

The twin-walled valve cover according to the present application can also be formed integrally with the valve housing or be a part that is welded on the valve housing. The twin-walled valve cover is formed by a cup-shaped part of the valve housing or the valve cover with a part of the valve housing forms a cup-shape. The cup-shape is in one possible embodiment constituted from a plurality of parts. These include a ring-shaped part of the valve housing as well as both walls of the valve cover. Both of the walls can be welded to the ring-shaped housing part or be connected in another manner.

The two walls are brought into the desired shape prior to welding. This can be carried out by pressing/deep drawing a planar material. Pressing/deep drawing in the cold state is possible for the desired state of strain.

The starting material for the walls of the valve cover can be deformed in one or more stages/steps. In a multi-stage production, a concentric corrugated structure is in one possible embodiment initially produced in the plane or with slight differences in height, prior to carrying out a final three-dimensional deformation in a second step.

A press is in one possible embodiment provided for the deformation. There are mechanically operated presses, hydraulic presses, and presses run by compressed air. The required or desired pressing force is low, because the leaf springs are small and thin. Therefore, manually operated presses, in one possible embodiment toggle presses, can be used.

The pressing tools comprise male and female molds. Separate male and female molds are provided for each deformation stage; accordingly, in a two-stage deformation process, a pair of male and female molds is used for the first deformation step, and another pair of male and female molds is used for the second deformation step.

With a molded outer wall, the inner wall that forms the abutment is in one possible embodiment matched to or similarly shaped as the outer wall. The molding required or desired for this does not have to identically or substantially identically reflect the shape of the outer wall. It is sufficient and involves less effort if the inner wall is provided with planar steps, onto which the outer wall comes into contact with its bulges. An inner wall can in one possible embodiment serve as an abutment for various outer walls.

The twin-walled design on the valve housing is also independent of the noise generation, likewise independently thereof of advantage, whether the axle, on which the rotating part is seated, is connected with the housing cover or forms a separate component.

The valves according to the present application in one possible embodiment have a diameter of eight millimeters to twenty millimeters, in another possible embodiment up to fifteen millimeters.

The size of the spring plate is optionally based on the size of the valve. However, a leaf spring of uniform size can be used for the valves. With larger valves the leaf spring is then incorporated into the valve cover.

The thickness of the leaf spring is in one possible embodiment chosen according to its diameter or according to its size. Leaf springs for a valve with a diameter of seventeen millimeters can have a thickness of, for example, less than or equal to 0.2 millimeters, or even less than or equal to 0.16 millimeters. For a smaller valve diameter and a correspondingly smaller leaf spring, the thickness can be less than or equal to 0.15 millimeters.

Whether and which deformation the leaf spring should receive depends on its function. In so far as the leaf spring is for unlocking the adjustment mechanism in a twin-walled design of the valve cover, then quite a small stroke of the leaf spring suffices to cancel out or disengage or overcome the friction lock between the rotating part/rotor and the valve cover. In some valves the required or desired stroke can be 0.1 millimeters or less. A stroke greater than 0.3 millimeters is generally not required or desired. For a small stroke the leaf spring does not have to be planished or given a smooth finish.

For the bulge according to the present application, the stroke designates the greatest distance between the two walls of a twin-walled valve cover construction. The greatest deformation path occurs at this point when the valve cover is pressed in. For a single wall valve cover construction, the stroke also designates the greatest deformation path of the valve cover.

A greater stroke is required or desired for an application of the twin-walled design according to the present application in order to produce a clicking noise, for example a stroke of at least 0.4 millimeters is required or desired for a valve diameter of seventeen millimeters. A greater or smaller stroke is required or desired depending on the diameter of the valve and size of the leaf spring, and depending on the desired noise generation, or depending on the extent of the snap-through of the bulge structure. In regard to the noise generation, the wishes of the patient and the perceptiveness of the physician in charge are to be taken into account. The smaller the stroke, the lower the noises. Moreover, a wave-shaped bulge structure can have a damping effect on the noise generation.

The stroke of the outer wall is in one possible embodiment 0.3 to two millimeters.

The desired stroke determines or contributes to determining the size of the permanent or substantially permanent bulge structure.

Various methods exist to produce the permanent or substantially permanent bulge structure. In the possible two-stage cold bending with the stamping of the wave form/bulge form, in the first bending step and the subsequent three-dimensional bending, the leaf spring is formed beyond the desired permanent or substantially permanent shape in order to take into account the elasticity of the leaf spring. The thinner the material used for the leaf springs, the more carefully the leaf springs should be shaped. This in one possible embodiment implies that the leaf springs in the second forming step are not further molded but rather deep-drawn. For deep-drawing, the leaf springs are clamped on the edge and bulged out with an appropriate molding part, such that the material can flow extremely well in the area of the permanent or substantially permanent shape.

For a use of the twin-walled valve cover with a bulge structure without noise generation, limitations associated with noise generation can be dispensed with. This applies in one possible embodiment to the limitation of the stroke in regard to sound damping.

Nonetheless, a signal still emanates from this type of valve, because the yielding of the outer wall of the valve cover can be felt by the treating physician.

Even with a single-wall design the valve covers can also be in one possible embodiment equipped with the above described bulge structure. Then, however, the thickness of the valve cover is such that by itself (without an abutment) it withstands the compression loads. The bulge structure according to the present application also offers possibilities in this application.

It is also possible if the rotating part/rotor is seated differently than on a known axle/pivot/bolt, which in regard to the flexible valve covers for locking and unlocking the rotating part/rotor, forms a separate component that is held in the valve housing and can slide longitudinally. The additional bearing that can slide longitudinally appears at first sight to be more costly than the integrally formed design with a valve cover. In a closer inspection, however, the separate design has constructional possibilities, in one possible embodiment in combination with a suddenly bulging noise-generating valve cover. Moreover, the valve with the movable bearing gains more possibilities in precision and operational reliability.

Furthermore, the use of an axle/pivot/bolt that is separate from the valve cover opens the possibility of a locking pressure that is produced independently of the housing deformation.

According to the present application the locking pressure is produced with an additionally provided spring. Various springs can be considered for this additional spring. In one possible embodiment, a spiral spring may be seated on the axle/pivot/bolt, with which the rotating part/rotor is driven. The spring has the possibility of a simpler dimensioning of the locking pressure. Moreover the locking pressure can easily be modified by changing the length of the spring or by replacing the spring.

A shorter stroke of the axle/pivot/bolt is required or desired for locking and unlocking. The stroke is in one possible embodiment limited.

For the limitation the axle/pivot/bolt can be equipped with a ring or flange. The ring is pressed on, for example. The flange is in one possible embodiment formed integrally with the axle/pivot/bolt.

The ring or flange cooperates with a stop in the housing.

The movement of the axle/pivot/bolt, on which the rotating part/rotor is seated, is in one possible embodiment limited by the valve floor on the valve that is located opposite the valve cover. In order to reduce at the same time the frictional force between the valve floor and the axle/pivot/bolt, this can be equipped on the side of the valve floor with a point.

Incidentally, the rotating part/rotor is, in one possible embodiment, provided with markings that, by means of X-rays or additional signals, provide information on the position of the rotating part/rotor. However, the information can also be produced by signals that are produced like the signals for locking/unlocking.

In case of doubt, it can be clarified by means of X-rays or by additional signals, whether the valve has been correctly or incorrectly implanted. Suitable markings are those that under X-rays, one side is distinguishable from the other side.

Bores in the rotating part/rotor are suitable markings if the bores are installed in an unmistakable manner and if the bores correlate distinctively with certain other housing features. Such a housing feature can be a stop for the rotating part/rotor or a feature on the valve inlet or on the valve outlet. Independently of the noise-generation of the present application and also independently of the above-described design/location of the present application of the rotating part/rotor, the markings can also be used in other designs of hydrocephalus valves.

A limitation of the rotational angle for the valve of the present application is also optionally provided. Bolts or studs or other stops in the housing can be provided for limiting the rotational movement.

In one possible embodiment, more than two magnets, for example four magnets, are also optionally provided on the rotor. This considerably increases the adjusting force on the rotor.

Finally, in one possible embodiment, dead spaces in the valve are eliminated or at least minimized or greatly restricted. In comparison to other cavities, dead spaces are cavities into which the fluid flows with a lower speed or even stagnates. Coagulates can easily form there.

The dangerous cavities can be eliminated or at least minimized in the area of the floor or cover by infilling. The cavity is, in one possible embodiment, filled in to the extent that the flow cross section between the fluid inlet and the fluid outlet is, on average, not more than ten square millimeters, in another possible embodiment, on average, not more than seven square millimeters, and in yet another possible embodiment, on average, not more than four square millimeters. Even better is if the flow cross section is never more than eight square millimeters at any point, in one possible embodiment not more than five square millimeters at any point, and in a further possible embodiment not more than three square millimeters at any point.

At the same time the flow cross section at any point between the fluid inlet and the valve gap between ball and ball seat, or between the valve gap and the fluid outlet, should not be less than the flow cross section in the fluid inlet. In contrast, the valve gap between ball and ball seat can be minimized or even reduced to zero if no excess fluid accrues.

The flow rate of the fluid in the valve should be increased with the design of the present application of the flow cross section.

A wafer-like rotating part/rotor can be possible for the desired design of the flow cross section if the fluid line runs along the peripheral surface of the rotating part/rotor. In this regard, channel-forming grooves/depressions can be provided in the peripheral surface of the rotating part/rotor and/or in the corresponding wall of the valve housing. The gap between rotating part/rotor and wall of the valve housing can be sealed in a conventional manner. The gap is in one possible embodiment designed so narrowly that the fluid cannot exit from the gap.

The above-discussed embodiments of the present invention will be described further herein below. When the word "invention" or "embodiment of the invention" is used in this specification, the word "invention" or "embodiment of the invention" includes "inventions" or "embodiments of the invention", that is the plural of "invention" or "embodiment of the invention". By stating "invention" or "embodiment of the invention", the Applicant does not in any way admit that the present application does not include more than one patentably and non-obviously distinct invention, and maintains that this application may include more than one patentably and non-obviously distinct invention. The Applicant hereby asserts that the disclosure of this application may include more than one invention, and, in the event that there is more than one invention, that these inventions may be patentable and non-obvious one with respect to the other.

BRIEF DESCRIPTION OF THE DRAWINGS

A possible embodiment of the present application is illustrated in the drawings, in which:

FIG. 7 shows a press for the production of a corrugated form in a wall for a twin-walled housing cover.

DESCRIPTION OF EMBODIMENT OR EMBODIMENTS

Figure 1:
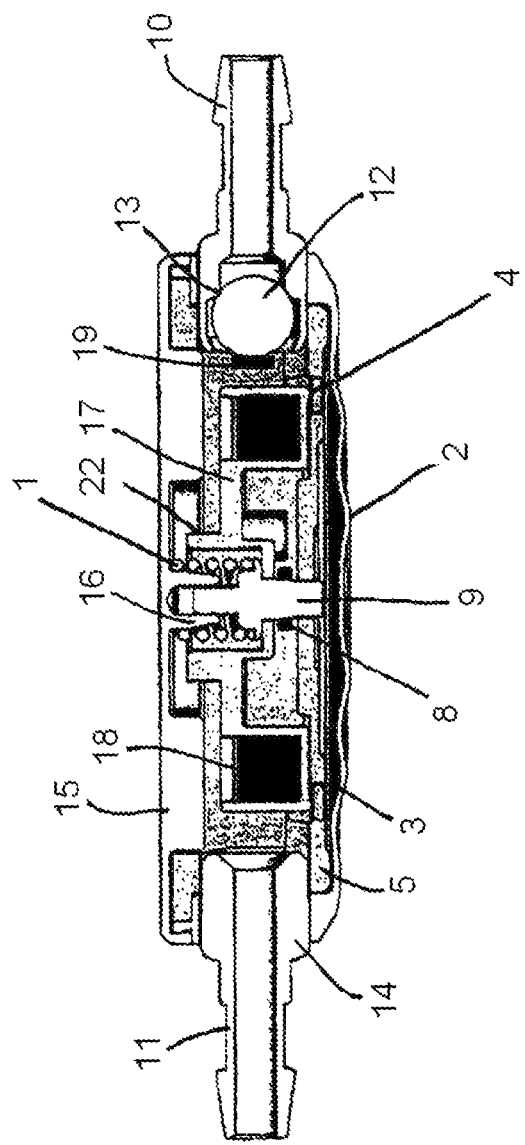
FIG. 1 shows a view of an adjustable valve according to the present application.
Figure 2:
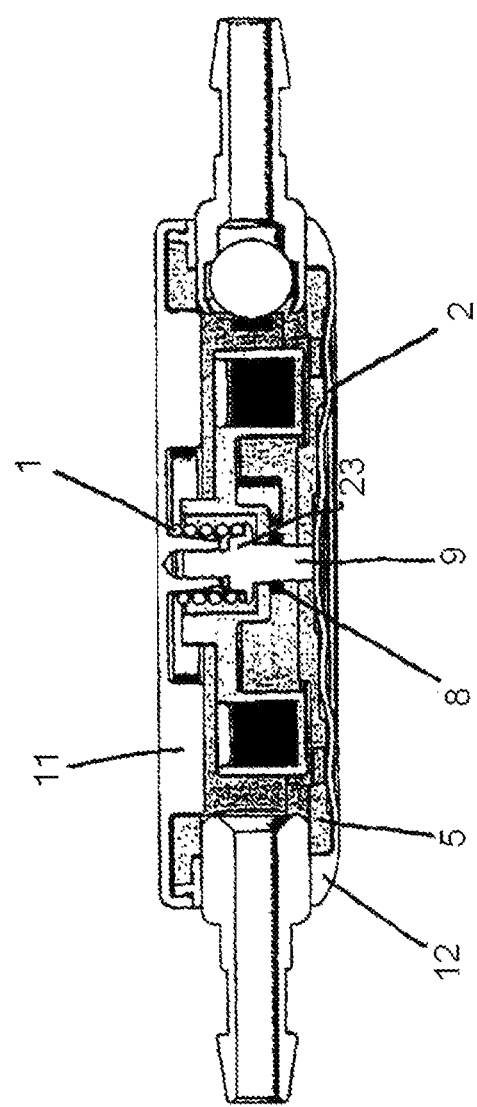
FIG. 2 shows another view of the adjustable valve shown in FIG. 1.

FIGS. 1 and 2 show similar sections through an adjustable valve according to the present application. In FIG. 1 the valve is locked, and in FIG. 2 the valve is unlocked for a valve adjustment.

The valve is located in a drain line for fluid. The inlet side of the valve is numbered 10 and the outlet side 11.

The valve has a housing, with a diameter of seventeen millimeters or about seventeen millimeters, which is composed of various parts. A housing ring is numbered 14, with a floor or wall 15 that closes the housing ring 14 on one side. Housing parts may be made of titanium (titanium alloys) and welded together. In other embodiments, housing parts are molded together, such that the housing is sealed tight.

The housing side that is opposite to the floor 15 of the housing is sealed by a twin-walled cover construction. The inner wall 5 provides the required or desired stability to this housing side and has still further functions that are mentioned below. The outer wall of the cover construction forms a manually deformable membrane/leaf spring 2. The outer wall/membrane/leaf spring 2 possesses a corrugated shape and, under external pressure, after reaching a labile central state, should suddenly bulge out against the inner wall/abutment 5. For this, the inner wall/abutment 5 is matched to the bulge that the outer wall/membrane/leaf spring 2 takes up. A stepped indentation toward the center of the valve is provided for the match. The inner wall 5 forms an abutment for the outer wall/membrane/leaf spring 2. As the abutment, the inner wall 5 limits the movement of the outer wall/membrane/leaf spring 2 when a physician presses with an adjustment device (not shown) externally on the skin of the patient against the outer wall/membrane/leaf spring 2.

Figure 3:
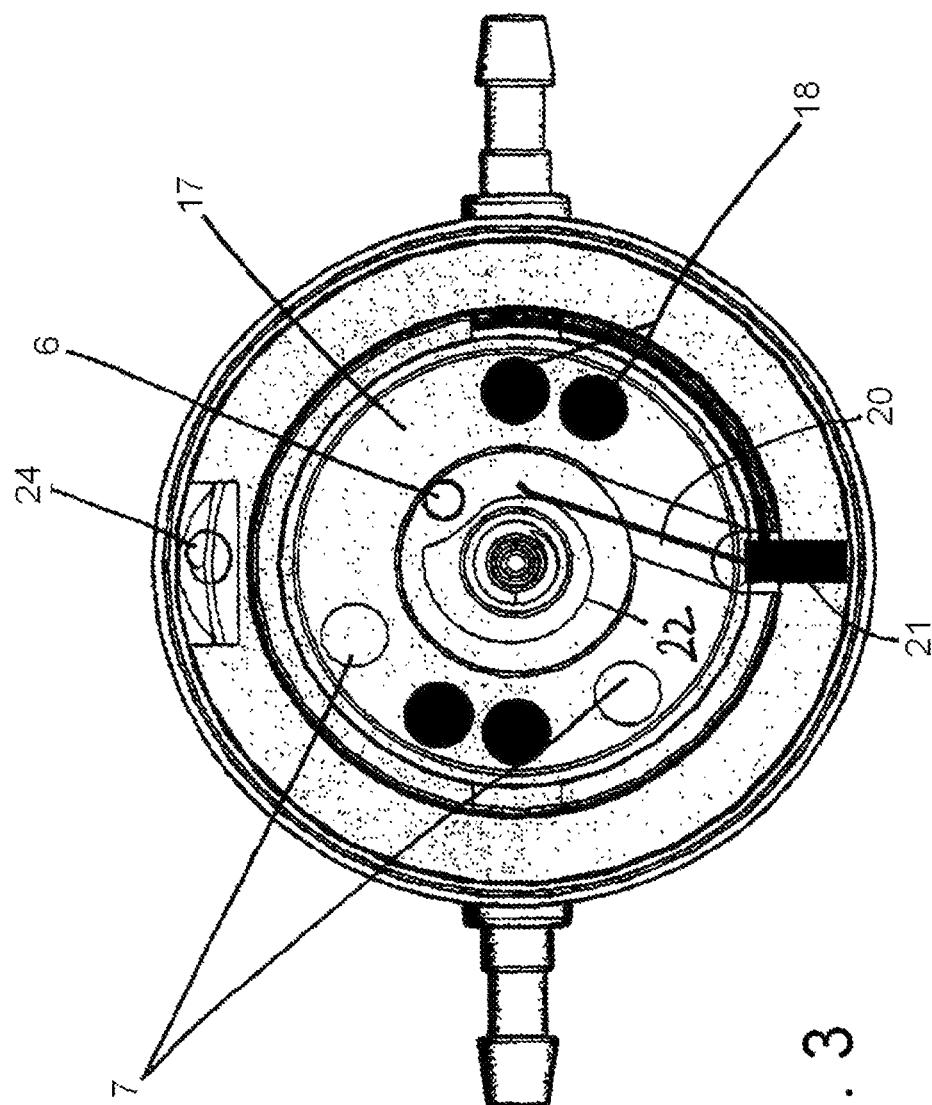
FIG. 3 shows a view of an adjustable valve according to the present application.
Figure 4:
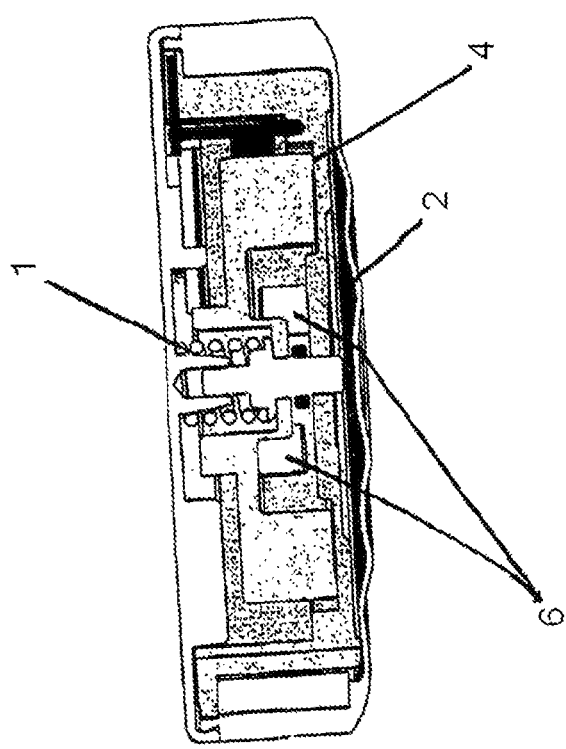
FIG. 4 shows a view of an adjustable valve according to the present application.

A valve ball 12, located in a valve seat 13, is provided on the inlet side in the housing. The reseating pressure of the valve ball is determined depending on the valve, by the weight of the ball and by a spring adjacent to the ball 12, or solely by the spring. One end 19 of the spring is illustrated in FIGS. 1 and 2. This concerns a leaf spring, whose end 19 according to FIG. 3 is guided in a curve to a rotatably movable fitting 21 for the spring. The curve is matched to the radius of curvature of the housing ring. The other end of the spring is numbered 20 and extends from the fitting 21 to a cam track 22 of a rotating part/rotor 17 that is rotatingly movably arranged in the housing. If the rotating part/rotor 17 of FIG. 2 has lifted off the inner wall/abutment 5, then the rotating part/rotor 17 can be rotated with the mentioned adjustment device. The spring end 20 thus experiences a bending or a moment of a torque, which, owing to the rotatably movable fitting 21, is transmitted to the other end of the spring 19 and leads to a modification of the closing pressure on the valve ball 12.

In the locking position of the valve according to FIG. 1, the rotatable part/rotor 17 is pressed against the inner wall/abutment 5. The wall/abutment 5 attains with its surface 3 a friction lock with the surface 4 of the adjustment part/rotor 17.

The locking pressure is produced by a spiral spring 1 that is supported at one end on the floor 15 and at the other end on a flange 23 of an axle 9. The axle 9 is axially slidable with one end and rotatably movably guided in a guide 16 of the valve floor 15. With the other end, the axle 9 is slidable and rotatably movably guided in a bearing bore 8 of the inner wall/abutment 5.

The rotating part/rotor 17 is seated on the axle 9, wherein the axle 9 is slidable in the axial direction in the rotating part/rotor 17. In the "locking" operating position according to FIG. 1, the rotor 17 is prevented or restricted from rotating by the frictional lock with the housing. This serves to secure the relevant valve position.

In the locking position, the axle 9 protrudes against the inner wall/abutment 5.

To release the lock, the outer wall/membrane/leaf spring 2 is pressed inward until the wall/membrane/leaf spring 2 and the axle 9 have taken up the position illustrated in FIG. 2. In this position the rotating part/rotor 17 has lifted off the inner wall/abutment 5.

On passing from the position in FIG. 1 to the position in FIG. 2, the outer wall/membrane/leaf spring 2 suddenly bulges out, that is, bulges against and/or toward the inner wall abutment 5, so as to move from a substantially convex shape in FIG. 1 to a substantially concave shape (or vice versa, depending on one's view) in FIG. 2. This leads to an acoustic signal, such as a click or clicking sound. Moreover, the movement is perceptible. The click and the perceptible resilience indicates to the treating physician that the lock has been released.

On unlocking, a ring deformed with the axle 9 essentially ensures or promotes that no excessive movement of the axle 9 occurs. Moreover, the outer wall/membrane/leaf spring 2 cannot move the axle 9 further than up to the inner wall/abutment 5. There, the upper end of the axle 9 locks with the inner wall/abutment.

After unlocking, the treating physician can use the above-mentioned adjustment device to turn the rotating part/rotor 17 on the axis 9 to a desired rotational position, thereby achieving a desired new closing pressure of the valve. The physician then relieves the strain on the outer wall/membrane/leaf spring 2. The pressure is removed from the membrane 2, such that the membrane can again recover the shape shown in FIG. 1. Under the pressure of the spring 1, the axle 9 is simultaneously or substantially simultaneously returned into the locking position and generates the friction lock required or desired for locking. The recovery of the outer wall/membrane/leaf spring produces another clicking sound that is understood by the treating physician as the locking signal.

For the purposes of generating the unlocking pressure, the treating physician uses the known, adjustment device (not shown), located externally on the body of the patient, to press against the center of the membrane 2. Adjustment devices of this type are known.

The adjustment device is equipped with magnets that interact with magnets 18 that are incorporated in the rotating part/rotor 17.

After unlocking, the treating physician rotates the adjustment device.

The rotation of the adjustment device is transferred through the magnets to the rotating part/rotor 17. In the embodiment four magnets 18 are located in the rotating part/rotor.

In the embodiment the rotational movement of the rotating part/rotor 17 is limited by arresters 6. The arresters 6 are pins. In other embodiments any other components can be employed as the arrester instead of the pins.

In the embodiment the rotating part/rotor 17 is moreover provided with markings that enable the treating physician to control the respective rotating part/rotor by X-raying. The markings concern the bores 7.

Finally, other markings 24 are applied to the housing and enable the control by X-rays of whether the valve has been correctly implanted.

Figure 5:
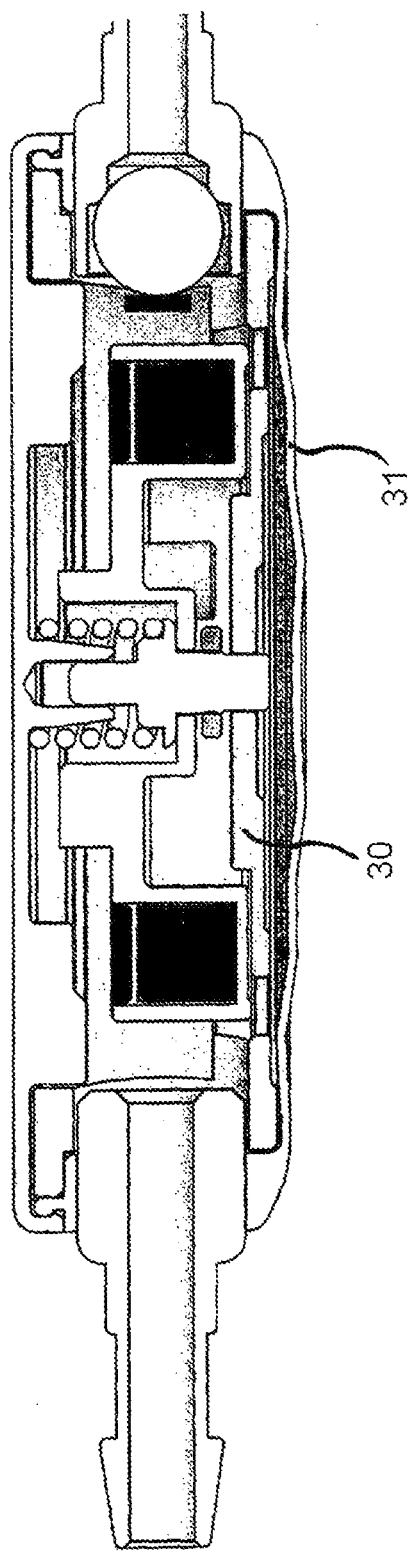
FIG. 5 shows a view of an adjustable valve with a twin-walled valve cover according to the present application.
Figure 6:
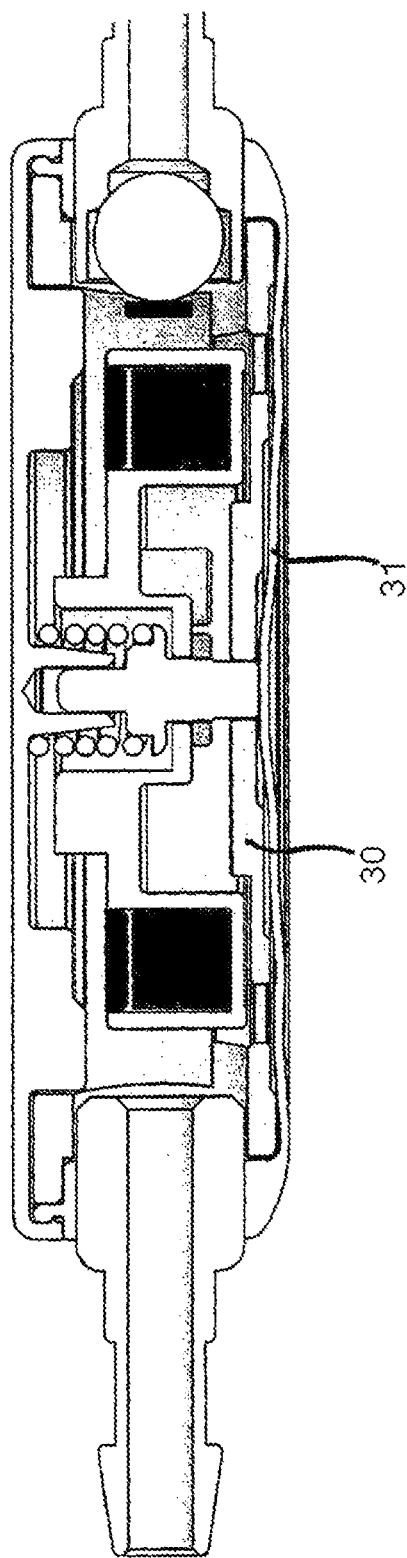
FIG. 6 shows a view of an adjustable valve with a twin-walled valve cover according to the present application.

FIGS. 5 and 6 show another hydrocephalus valve with a twin-walled valve cover. In other components, the valve of FIGS. 5 and 6 corresponds with the valve of FIGS. 1 to 4.

In the twin-walled valve cover, the inner wall/abutment 30 corresponds to the inner wall/abutment 5 of FIGS. 1 to 4. A difference arises with the outer wall/membrane/leaf spring 31.

A bulge structure is provided in the outer wall/membrane/leaf spring 31 and is characterized in the starting position of FIG. 5 by a stepped bulge. Bulging surfaces that run planar and parallel or substantially parallel to the floor of the valve housing are provided in each step. Obliquely running transition surfaces are provided between the various steps. The illustrated bulges can be more easily worked into the starting material than the corrugated structure of FIGS. 1 to 4.

FIG. 7 shows a press for the production of a corrugated form in a wall for a twin-walled housing cover made of a titanium alloy. In this regard, the wall in the example comprises a circular film 41, with a thickness of 0.15 millimeters or about 0.15 millimeters, and a ring 42. In the embodiment the film 41 is manufactured with the ring 42 in one piece as a turned part on a lathe. In other embodiments the film 41 and the ring 42 are manufactured as separate parts and are welded together. A cup-shaped wall for a twin-walled housing cover with a planar surface is formed by the linkage. The diameter of the film is 14.6 millimeters or about 14.6 millimeters. After bulging out, the wall as the outer wall with a second wall as the inner wall is joined to a cover. The cover is destined for a hydrocephalus valve with a diameter of seventeen millimeters or about seventeen millimeters.

In the illustrated starting shape the outer wall, prior to the connection with the inner wall, is furnished with a bulge structure. For this, the wall lies in a press comprising a female mold 43 and a male mold 44. The male mold and the female mold possess bulges 45 and recesses 46. In this regard, each bulge 45 lies opposite a recess 46. Moreover, a central bulge 47 is provided that lies opposite a central recess 48. FIG. 7 comprises a sectional view, so that each two bulges 45 with the same distance to the center of the wall belong to a circle on the female mold and on the male mold.

Accordingly, each two recesses with the same distance to the center of the wall also belong to a circular recess.

In a first molding step the female mold and the male mold are moved against one another, such that the bulges 45 press against the film 41 and 0.5 millimeters, or about 0.5 millimeters, high corrugations are created.

The shape of the molded corrugations depends on the curvature of the bulges 45 on their contact surface with the film 41. With large curvatures, sinusoidal corrugations can be created for example. With small (sharp) curvatures, approximately zig-zag shaped corrugations are formed.

In the embodiment, after the film has been released by retracting the female and male molds, corrugations remain with a height of about 0.25 millimeters. The film 41 then becomes much more flexible. Under a load of one kilogram, the molded film 41 bulges out by 0.2 millimeters, whereas an unaltered, planar film 41 bulges out by 0.1 millimeters.

In a second molding step the wall is bulged out by an additional one millimeter. In the unloaded condition, the film 41 then bulges out by 0.3 millimeters.

The resulting wall (of the ring 42 and film 41) can be pressed in by 0.6 millimeters with a centrally applied force of six to seven Newtons. This results in a clicking noise. After being pressed in, the resulting wall returns automatically into the initial shape when the strain on the wall is again relieved.

In the application with twin-walled valve cover constructions as in FIGS. 1 to 6, an automatic return of the outer wall into the initial shape after indentation may not be necessary or desired, because an indentation of the outer wall has to be performed against a spring force, which after relieving the outer wall from the pressure of the adjustment device, the compressed spring initiates the return/shape recovery of the outer wall into the initial shape. However, the automatic return forms a possible security for the return/shape recovery of the outer wall.

In embodiments of outer walls for valve covers with another diameter, thinner films are used for smaller diameters and thicker films are used for larger diameters. For this, the film thickness is modified for example in steps of a few hundredths of millimeters in order to obtain comparable results under otherwise equal circumstances.

It should be noted that all measurements listed herein are for exemplary purposes or to describe at least one possible embodiment. Other possible embodiments could include components of different measurements that could be less than or greater than the listed measurements.

Some examples of equipment relating to the treatment of hydrocephalus may be found in the following patent publications, which are incorporated by reference as if set forth in their entirety herein: DE 60024437 T2, having the title "Tool for Adjusting an Implantable Adjustable Fluid Flow Control Valve," published on Jul. 13, 2006; DE 60315924 T2, having the title "Shunt valve locking mechanism," published on May 21, 2008; DE 69808558 T2, having the title "Pediatric programmable hydrocephalus valve," published on Jun. 26, 2003; EP 1243826 A2, having the title "Pressure-variable valve device and set-pressure adjusting device for the valve device," published on Sep. 25, 2002; EP 1457231 B1, having the title "Implantable valve for the treatment of hydrocephalus," published on Sep. 15, 2004; EP 1604703 B1, having the title "Valve for subcutaneous use," published on Dec. 14, 2005; EP 1642613 B1, having the title "High pressure range hydrocephalus valve system," published on Apr. 5, 2006; EP 2420284 A2, having the title "Implantable adjustable valve," published on Feb. 22, 2012; U.S. Pat. No. 4,443,214, having the title "Valve for the treatment of hydrocephalus," published on Apr. 17, 1984; U.S. Pat. No. 4,540,400, having the title "Non-invasively adjustable valve," published on Sep. 10, 1985; U.S. Pat. No. 4,551,128, having the title "Cerebrospinal fluid shunt valve," published on Nov. 5, 1985; U.S. Pat. No. 4,673,384, having the title "Valve for the treatment of hydrocephalus," published on Jun. 16, 1987; U.S. Pat. No. 4,769,002, having the title "Intercranial pressure regulator valve," published on Sep. 6, 1988; U.S. Pat. No. 5,843,013, having the title "Valve for the treatment of hydrocephalus," published on Dec. 1, 1998; U.S. Pat. No. 6,840,917, having the title "Implantable subcutaneous valve for the treatment of hydrocephalus, and adjusting devices therefor," published on Jan. 11, 2005; U.S. Pat. No. 8,298,168, having the title "ADJUSTMENT FOR HYDROCEPHALUS SHUNT VALVE," published on Oct. 30, 2012; US 2005/0055009, having the title "Method and apparatus for managing normal pressure hydrocephalus," published on Mar. 10, 2005; US 2012/0197178, having the title "READING AND ADJUSTING TOOL FOR HYDROCEPHALUS SHUNT VALVE," published on Aug. 2, 2012; US 2012/0302937, having the title "Programmable Device For Treating Over Drainage Due To Siphonic Effects In Hydrocephalus Shunt Systems," published on Nov. 29, 2012; US 2013/0066253, having the title "ADJUSTMENT FOR HYDROCEPHALUS SHUNT VALVE," published on Mar. 14, 2013; US 2013/0085441, having the title "SHUNT VALVE FOR TREATMENT OF HYDROCEPHALUS," published on Apr. 4, 2013; DE 10358145, having the title "Adjustable hydrocephalus valve for pressure compensation in the cranium of a hydrocephalus patient by drainage of excess cerebral liquor into the peritoneum or heart comprises a spring and a mechanically and percutaneously activated brake," published on Jul. 1, 2004; DE 102008030942, having the title "CEREBROSPINAL FLUID DRAINAGE," published on Jan. 7, 2010; and US 2014/0005569, having the title "IMPLANT FOR MEASURING THE INTRACORPOREAL PRESSURE WITH TELEMETRIC TRANSMISSION OF THE MEASURED VALUE," published on Jan. 2, 2014.

The present application relates to an adjustable hydrocephalus valve, which can be locked in the respective selected valve position and unlocked for modifying the valve position. According to the present application, signals are provided for a treating physician in the event that an unlocking and another locking occur.

One feature or aspect of an embodiment is believed at the time of the filing of this patent application to possibly reside broadly in an adjustable hydrocephalus valve for pressure equalization of the fluid in the cranium of a hydrocephalus patient, wherein the valve is implantable in the patient and is in one possible embodiment drainable with a likewise implantable tube line, through which excess fluid can be withdrawn from the cranium of the patient into the upper vena cava or into the abdominal cavity, wherein the valve pressure is determined by a spring and wherein the spring is adjusted by an adjusting mechanism, such that the spring is wound up or released, wherein the adjusting mechanism of the valve possesses a pivotably movable or rotatably movable rotating part/rotor located in the valve, said rotor being equipped with magnets and can be moved from the exterior by pivoting or turning an adjustment device that is itself equipped with magnets, wherein the valve is equipped with a locking device for the rotating part/rotor, such that between two adjustment procedures the rotating part/rotor can be locked in place, and wherein the locking occurs by friction and/or by a tooth system between the rotating part/rotor and the housing and wherein the pivotably movable or rotatably movable rotating part/rotor can be moved in the axial direction by pressing down on the valve cover so as to release the friction lock or to release the meshed teeth, wherein the unlocking movement occurs against a spring force that on locking causes the frictional lock or the teeth to mesh, wherein the valve is equipped with a signaling device for the unlocking and/or locking and/or the valve cover is constructed with at least two walls and/or the valve cover is equipped with a compressible bulge and/or the valve is equipped with a spring that is independent of the housing deformation and that brings about the frictional lock or the meshing of the teeth and/or the rotating part/rotor is arranged on an axle that in relation to the deformable valve cover forms a separate component in the valve.

Another feature or aspect of an embodiment is believed at the time of the filing of this patent application to possibly reside broadly in the valve, which valve comprises acoustic and/or optical and/or perceptible signals.

Yet another feature or aspect of an embodiment is believed at the time of the filing of this patent application to possibly reside broadly in the valve, which valve comprises a mechanical and/or electronic signal generator.

Still another feature or aspect of an embodiment is believed at the time of the filing of this patent application to possibly reside broadly in the valve, which valve comprises a compressible bulge of the valve cover which can at least be brought into a metastable state.

A further feature or aspect of an embodiment is believed at the time of the filing of this patent application to possibly reside broadly in the valve, which valve comprises a multi-step deformation of the valve cover.

Another feature or aspect of an embodiment is believed at the time of the filing of this patent application to possibly reside broadly in the valve, wherein a stable opposing bulge can be produced by compression, and with counter-pressure the opposing bulge can be reformed into the original bulge or that the opposing bulge automatically reverts into the original bulge in the valve cover due to the internal stress condition.

Yet another feature or aspect of an embodiment is believed at the time of the filing of this patent application to possibly reside broadly in the valve, wherein the valve cover is constructed with at least two walls, wherein the external wall is compressible and the inner wall forms an abutment for the external wall.

Still another feature or aspect of an embodiment is believed at the time of the filing of this patent application to possibly reside broadly in the valve, wherein the travel of the external wall is less than the travel for the formation of a stable opposing bulge.

A further feature or aspect of an embodiment is believed at the time of the filing of this patent application to possibly reside broadly in the valve, wherein with a two-walled valve cover the inner wall limits the travel of the external wall.

Another feature or aspect of an embodiment is believed at the time of the filing of this patent application to possibly reside broadly in the valve, wherein the pivotably movable or rotatably movable rotating part/rotor is pivotably or rotatably mounted with an axle, pivot or bolt and that the axle/pivot/bolt at the same time is displaceably arranged in the axial direction, wherein a displacement path in the one axial direction has one end position and a displacement path in the opposite axial direction has a second end position, wherein with the displacement the one end position is the unlocking position and the other end position is the locking position.

Yet another feature or aspect of an embodiment is believed at the time of the filing of this patent application to possibly reside broadly in the valve, wherein a spring is provided as the drive for the displacement into the locking position, the spring being independent from the drive for the displacement into the unlocking position.

Still another feature or aspect of an embodiment is believed at the time of the filing of this patent application to possibly reside broadly in the valve, wherein the adjusting device that is arranged externally on the body of the patient is provided as the drive for the displacement into the unlocking position.

A further feature or aspect of an embodiment is believed at the time of the filing of this patent application to possibly reside broadly in the valve, wherein in the unlocking position the end of the axle, pivot or bolt on the side of the valve cover is flush with the surface of the inner wall of the two-walled valve cover, and in the locking position protrudes outwards toward the surface of the inner wall.

One feature or aspect of an embodiment is believed at the time of the filing of this patent application to possibly reside broadly in the valve, wherein the pivotably movable or rotatably movable rotating part/rotor located inside the valve possesses at least one bore for determining the position of the rotating part/rotor.

Another feature or aspect of an embodiment is believed at the time of the filing of this patent application to possibly reside broadly in the valve, where the location of the rotating part/rotor being determined by X-rays.

Yet another feature or aspect of an embodiment is believed at the time of the filing of this patent application to possibly reside broadly in the valve, wherein limit stops in the valve for limiting the rotational movement of the rotating part/rotor, in one possible embodiment by pivots as the limit stops.

Still another feature or aspect of an embodiment is believed at the time of the filing of this patent application to possibly reside broadly in the valve, which valve comprises a marking on the valve for determining the location of the implant.

A further feature or aspect of an embodiment is believed at the time of the filing of this patent application to possibly reside broadly in the valve, wherein the location of the implant being determined by X-rays.

The components disclosed in the patents, patent applications, patent publications, and other documents disclosed or incorporated by reference herein, may possibly be used in possible embodiments of the present invention, as well as equivalents thereof.

The purpose of the statements about the technical field is generally to enable the Patent and Trademark Office and the public to determine quickly, from a cursory inspection, the nature of this patent application. The description of the technical field is believed, at the time of the filing of this patent application, to adequately describe the technical field of this patent application. However, the description of the technical field may not be completely applicable to the claims as originally filed in this patent application, as amended during prosecution of this patent application, and as ultimately allowed in any patent issuing from this patent application. Therefore, any statements made relating to the technical field are not intended to limit the claims in any manner and should not be interpreted as limiting the claims in any manner.

The appended drawings in their entirety, including all dimensions, proportions and/or shapes in at least one embodiment of the invention, are accurate and are hereby included by reference into this specification.

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

All, or substantially all, of the components and methods of the various embodiments may be used with at least one embodiment or all of the embodiments, if more than one embodiment is described herein.

The purpose of the statements about the object or objects is generally to enable the Patent and Trademark Office and the public to determine quickly, from a cursory inspection, the nature of this patent application. The description of the object or objects is believed, at the time of the filing of this patent application, to adequately describe the object or objects of this patent application. However, the description of the object or objects may not be completely applicable to the claims as originally filed in this patent application, as amended during prosecution of this patent application, and as ultimately allowed in any patent issuing from this patent application. Therefore, any statements made relating to the object or objects are not intended to limit the claims in any manner and should not be interpreted as limiting the claims in any manner.

All of the patents, patent applications, patent publications, and other documents cited herein, and in the Declaration attached hereto, are hereby incorporated by reference as if set forth in their entirety herein except for the exceptions indicated herein.

The summary is believed, at the time of the filing of this patent application, to adequately summarize this patent application. However, portions or all of the information contained in the summary may not be completely applicable to the claims as originally filed in this patent application, as amended during prosecution of this patent application, and as ultimately allowed in any patent issuing from this patent application. Therefore, any statements made relating to the summary are not intended to limit the claims in any manner and should not be interpreted as limiting the claims in any manner.

It will be understood that the examples of patents, patent applications, patent publications, and other documents which are included in this application and which are referred to in paragraphs which state "Some examples of . . . which may possibly be used in at least one possible embodiment of the present application . . . " may possibly not be used or useable in any one or more embodiments of the application.

The sentence immediately above relates to patents, patent applications, patent publications, and other documents either incorporated by reference or not incorporated by reference.

All of the patents, patent applications, patent publications, and other documents, except for the exceptions indicated herein, which were cited in the International Search Report dated Feb. 6, 2014, and/or cited elsewhere, as well as the International Search Report document itself, are hereby incorporated by reference as if set forth in their entirety herein except for the exceptions indicated herein, as follows: DE 10 2005 013720, having the title "Adjustable hydrocephalus valve for pressure equalization of liquor in skull of patient of hydrocephalus, and for use in adjusting system, is implanted to patient via hose line," published on Aug. 2, 2012; and U.S. Pat. No. 5,637,083, having the title "Implantable adjustable fluid flow control valve," published on Jun. 10, 1997.

The corresponding foreign and international patent publication applications, namely, Federal Republic of Germany Patent Application No. 10 2012 017 886.7, filed on Sep. 11, 2012, having inventor Christoph MIETHKE, and DE-OS 10 2012 017 886.7 and DE-PS 10 2012 017 886.7, and International Application No. PCT/EP2013/002713, filed on Sep. 10, 2013, having WIPO Publication No. WO 2014/040723 and inventor Christoph MIETHKE, are hereby incorporated by reference as if set forth in their entirety herein, except for the exceptions indicated herein, for the purpose of correcting and explaining any possible misinterpretations of the English translation thereof. In addition, the published equivalents of the above corresponding foreign and international patent publication applications, and other equivalents or corresponding applications, if any, in corresponding cases in the Federal Republic of Germany and elsewhere, and the references and documents cited in any of the documents cited herein, such as the patents, patent applications, patent publications, and other documents, except for the exceptions indicated herein, are hereby incorporated by reference as if set forth in their entirety herein except for the exceptions indicated herein.

The purpose of incorporating the corresponding foreign equivalent patent application(s), that is, PCT/EP2013/002713 and German Patent Application 10 2012 017 886.7, is solely for the purposes of providing a basis of correction of any wording in the pages of the present application, which may have been mistranslated or misinterpreted by the translator, and to provide additional information relating to technical features of one or more embodiments, which information may not be completely disclosed in the wording in the pages of this application.

Statements made in the original foreign patent applications PCT/EP2013/002713 and DE 10 2012 017 886.7 from which this patent application claims priority which do not have to do with the correction of the translation in this patent application are not to be included in this patent application in the incorporation by reference.

Any statements about admissions of prior art in the original foreign patent applications PCT/EP2013/002713 and DE 10 2012 017 886.7 are not to be included in this patent application in the incorporation by reference, since the laws relating to prior art in non-U.S. Patent Offices and courts may be substantially different from the Patent Laws of the United States.

All of the references and documents cited in any of the patents, patent applications, patent publications, and other documents cited herein, except for the exceptions indicated herein, are hereby incorporated by reference as if set forth in their entirety herein except for the exceptions indicated herein. All of the patents, patent applications, patent publications, and other documents cited herein, referred to in the immediately preceding sentence, include all of the patents, patent applications, patent publications, and other documents cited anywhere in the present application.

Words relating to the opinions and judgments of the author of all patents, patent applications, patent publications, and other documents cited herein and not directly relating to the technical details of the description of the embodiments therein are not incorporated by reference.

The words all, always, absolutely, consistently, preferably, guarantee, particularly, constantly, ensure, necessarily, immediately, endlessly, avoid, exactly, continually, expediently, ideal, need, must, only, perpetual, precise, perfect, require, requisite, simultaneous, total, unavoidable, and unnecessary, or words substantially equivalent to the above-mentioned words in this sentence, when not used to describe technical features of one or more embodiments of the patents, patent applications, patent publications, and other documents, are not considered to be incorporated by reference herein for any of the patents, patent applications, patent publications, and other documents cited herein.

The description of the embodiment or embodiments is believed, at the time of the filing of this patent application, to adequately describe the embodiment or embodiments of this patent application. However, portions of the description of the embodiment or embodiments may not be completely applicable to the claims as originally filed in this patent application, as amended during prosecution of this patent application, and as ultimately allowed in any patent issuing from this patent application. Therefore, any statements made relating to the embodiment or embodiments are not intended to limit the claims in any manner and should not be interpreted as limiting the claims in any manner.

The details in the patents, patent applications, patent publications, and other documents cited herein may be considered to be incorporable, at applicant's option, into the claims during prosecution as further limitations in the claims to patentably distinguish any amended claims from any applied prior art.

The purpose of the title of this patent application is generally to enable the Patent and Trademark Office and the public to determine quickly, from a cursory inspection, the nature of this patent application. The title is believed, at the time of the filing of this patent application, to adequately reflect the general nature of this patent application. However, the title may not be completely applicable to the technical field, the object or objects, the summary, the description of the embodiment or embodiments, and the claims as originally filed in this patent application, as amended during prosecution of this patent application, and as ultimately allowed in any patent issuing from this patent application. Therefore, the title is not intended to limit the claims in any manner and should not be interpreted as limiting the claims in any manner.

The abstract of the disclosure is submitted herewith as required by 37 C.F.R. §1.72(b). As stated in 37 C.F.R. §1.72(b):

A brief abstract of the technical disclosure in the specification must commence on a separate sheet, preferably following the claims, under the heading "Abstract of the Disclosure." The purpose of the abstract is to enable the Patent and Trademark Office and the public generally to determine quickly from a cursory inspection the nature and gist of the technical disclosure. The abstract shall not be used for interpreting the scope of the claims.

Therefore, any statements made relating to the abstract are not intended to limit the claims in any manner and should not be interpreted as limiting the claims in any manner.

The embodiments of the invention described herein above in the context of the preferred embodiments are not to be taken as limiting the embodiments of the invention to all of the provided details thereof, since modifications and variations thereof may be made without departing from the spirit and scope of the embodiments of the invention.

What is claimed is:

1. An adjustable hydrocephalus valve for pressure equalization of the cerebrospinal fluid in the cranium of a hydrocephalus patient, which said valve is implantable in a patient and controls drainage of excess cerebrospinal fluid, said valve comprising:

an inlet, an outlet, and a housing through which cerebrospinal fluid flows between said inlet and said outlet;

a spring disposed in said housing and configured to set the opening and closing pressure of said valve;

an adjusting mechanism disposed in said housing and comprising a rotatable part configured to be rotated to adjust a pressure force exerted by said spring;

at least one of said rotatable part and said housing comprising a locking device, which locking device comprises at least one of: frictional surfaces and locking teeth;

said rotatable part and said housing being configured to engage with one another to thereby engage said locking device and lock said rotatable part in a desired position between adjustments;

said housing comprising a cover portion configured to be depressed to displace at least a portion of said rotatable part along its rotational axis, and to thereby disengage said locking device to permit rotation of said rotatable part;

said cover portion being configured and disposed to bulge outwardly in a substantially convex shape, and being configured to bulge inwardly in a substantially concave shape upon being depressed toward the interior of said housing;

said cover portion being configured to snap between said outward bulge and said inward bulge to thereby generate an audio and/or visual signal indicating that said cover portion has been one of (A) and (B):
  (A) switched from said outward bulge to said inward bulge to alert a user that said rotatable part has been disengaged from said locking part to permit rotation of said rotatable part; and
  (B) switched from said inward bulge to said outward bulge to alert a user that said rotatable part has been engaged with said locking part to lock said rotatable part in place;

said valve comprises a second spring configured to bias said rotatable part against said locking device to lock said rotatable part in a desired position;

said cover portion is configured to be depressed to thereby displace said rotatable part along its rotational axis against the biasing force of said second spring; and one of (C) and (D):
  (C) said second spring is configured to press said cover portion from said inward bulge to said outward bulge upon termination of a depressing force on said cover portion; and
  (D) said cover portion is configured to be sufficiently resilient to automatically move on its own from said inward bulge to said outward bulge upon termination of a depressing force on said cover portion.

2. An adjustable hydrocephalus valve for pressure equalization of the cerebrospinal fluid in the cranium of a hydrocephalus patient, which said valve is implantable in a patient and controls drainage of excess cerebrospinal fluid from the cranium of the patient into the upper vena cava or into the abdominal cavity, said valve comprising:

an inlet, an outlet, and a housing through which cerebrospinal fluid flows between said inlet and said outlet;

a spring configured to determine the valve pressure;

an adjusting mechanism configured to adjust said spring to wind up or release said spring;

said adjusting mechanism comprising a pivotably movable or rotatably movable rotatable part;

said rotatable part comprising magnets configured to permit pivoting or turning of said rotatable part from outside said valve by a magnetic adjustment device;

at least one of said rotatable part and said housing comprising a locking device, which locking device comprises at least one of: frictional surfaces and locking teeth;

said rotatable part and said housing being configured to engage with one another to thereby engage said locking device and lock said rotatable part in a desired position between adjustments;

said housing comprising a cover portion configured to be depressed to displace at least a portion of said rotatable part along its rotational axis, and to thereby disengage said locking device to permit rotation of said rotatable part;

said cover portion being compressible and disposed to bulge outwardly;

said cover portion being configured to at least be brought into a metastable state; and wherein at least one of (A)-(E):
  (A) said cover portion being configured to generate acoustic and/or optical signals sufficient to be perceived by a person adjusting said valve and/or unlocking or locking said rotatable part;
  (B) said valve further comprising a mechanical and/or electronic signal generator;
  (C) said cover portion comprising at least two walls;
  (D) said valve further comprising a spring being configured to bring about locking engagement of said rotatable part and said housing; and
  (E) said rotatable part being disposed on an axle that is separate from said cover portion.

3. The valve according to claim 2, wherein:
said cover portion being configured to bulge inwardly in a substantially concave shape upon being depressed toward the interior of said housing; and
said valve comprises a pressure device configured to press said cover portion from said inward bulge to said outward bulge, or said cover portion is sufficiently resilient to move on its own from said inward bulge to said outward bulge.

4. The valve according to claim 3, wherein said valve cover comprise an inner wall and an outer wall, wherein said outer wall is compressible and said inner wall forms an abutment for said outer wall.

5. The valve according to claim 4, wherein said outer wall is configured to move less than a distance of movement sufficient for the formation of a stable inward bulge.

6. The valve according to claim 5, wherein with a two-walled valve cover, said inner wall limits movement of said outer wall.

7. The valve according to claim 2, wherein:
said rotatable part is pivotably or rotatably mounted on a support structure comprising an axle, pivot, or bolt; and
said support structure is configured to be displaced in a first axial direction to an unlocked position, and is configured to be displaced in an opposite, second axial direction to a locked position.

8. The valve according to claim 7, wherein said valve comprises a second spring configured to exert a biasing force to displace said support structure into the locked position.

9. The valve according to claim 8, wherein said support structure is configured to be displaced into the unlocked position by an external adjusting device, against the biasing force of said second spring.

10. The valve according to claim 9, wherein:
said valve cover comprise an inner wall and an outer wall; and
upon said support structure being in said unlocked position, an end of said support structure is disposed flush with said inner wall, and, upon said support structure being in said locked position, said end of said support structure protrudes beyond said inner wall.

11. The valve according to claim 2, wherein said rotatable part located comprises at least one bore for determining the position of the rotatable part.

12. The valve according to claim 11, wherein said valve comprises limit stops configured to limit rotational movement of said rotatable part.

13. The valve according to claim 12, wherein said valve comprises a marking for determining the location of said valve in a patient.

\* \* \* \* \*